United States Patent [19]

Singhbansal et al.

[11] Patent Number: 5,466,662
[45] Date of Patent: Nov. 14, 1995

[54] USE OF 4-CHLORO-3-(4-CHLORO-2-FLUOROPHENYL)-5-DIFLUOROMETHOXY-1-METHYL-1H-PYRAZOLE AS AN HERBICIDAL TREATMENT

[75] Inventors: Harjinder Singhbansal, Bracknell; John C. Ormrod, Farnborough, both of United Kingdom

[73] Assignee: Zeneca Limited, London, United Kingdom

[21] Appl. No.: 233,191

[22] Filed: Apr. 26, 1994

[30] Foreign Application Priority Data

May 10, 1993 [GB] United Kingdom ............ 9309542

[51] Int. Cl.⁶ ........................................ A01N 43/56
[52] U.S. Cl. ........................................ 504/202; 504/139
[58] Field of Search .............................. 504/282

[56] References Cited

FOREIGN PATENT DOCUMENTS 0443059  8/1991  European Pat. Off. .
03072460  3/1991  Japan .

OTHER PUBLICATIONS

Chemical Abstracts, vol. 118, No. 5, 12 Apr. 1993, Abstract No. 147554.

*Primary Examiner*—Richard L. Raymond
*Assistant Examiner*—Brian Bembenick
*Attorney, Agent, or Firm*—Marian T. Thomson

[57] ABSTRACT

A method for killing or controlling weeds in a soya crop, which method comprises applying to the crop or to the location thereof a compound of formula (I):

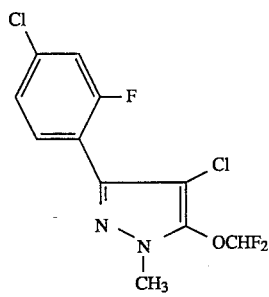

in an amount sufficient to kill the weeds but insufficient to kill the crop.

21 Claims, No Drawings

USE OF 4-CHLORO-3-(4-CHLORO-2-FLUOROPHENYL)-5-DIFLUOROMETHOXY-1-METHYL-1H-PYRAZOLE AS AN HERBICIDAL TREATMENT

The present invention relates to a herbicidal compound which has been found to have exceptional properties as a selective herbicide when used in soya crops.

Japanese Patent application No. J03072460 describes a series of herbicidal 3-substituted-phenylpyrazole derivatives. The applicants have found that one of these compounds has exceptional properties as a soya selective herbicide. Selectivity in corn has also been noted.

According to the present invention there is provided a method for killing or controlling weeds in a soya crop, which method comprises applying to the crop or to the location thereof a compound of formula (I) in an amount sufficient to kill the weeds but insufficient to kill the crop.

The compound of formula (I) is useful for the control of many weed species, in particular Ipomoea species, Amaranthus species, Datura species, Euphorbia species, Sida species, Setaria species, Echinochloa species, Sorghum species, Brachiaria species, Panicum species, Solanum species, Digitaria species, Xanthium species, Polygonum species, *Chenopodium album* and *Abutilon threophrasti*. Specific weeds which are controlled or suppressed by the compound of formula (I) include *Chenopodium album, Amaranthus retroflexus, Euphorbia heterophylla*, Ipomoea species, *Xanthium strumarium, Avena fatua, Alopecurus myosuroides, Agropyron repens, Sorghum halepense, Setaria viridis, Brachiaria platyphylla, Panicum dicotomiflorum, Panicum miliaceum, Echinochloa crus-galli, Cyperus esculentus, Abutilon threophrasti, Sida spinosa, Solanum nigrum, Setaria faberii, Setaria lutescens, Digitalia sanguinalis, Sorghum vulgare, Polygonum aviculare, Matricaria perforata* and *Galium aparine*. More especially the compound is useful for controlling *Abutilon threophrasti, Euphorbia heterophylla*, Ipomoea species, *Chenopodium album, Amaranthus retroflexus, Sida spinosa, Solanum nigrum, Setaria faberii, Setaria viridis, Echinochloa crus-galli, Digitaria sanguinalis, Panicum dicotomiflorum, Panicum miliaceum, Sorghum halepense, Brachiaria platyphylla, Sorghum vulgare* and *Setaria lutescens*.

The preparation of the compound of formula (I) is described in J03072460.

The compound of formula (I) may be applied directly to the plant (post-emergence application) or to the soil before the emergence of the plant (pre-emergence application). It is particularly useful when applied pre-emergence.

The compound of formula (I) may be used on its own to inhibit the growth of, severely damage, or kill plants but is preferably used in the form of a composition comprising a compound of formula (I) in admixture with a carrier comprising a solid or liquid diluent.

Therefore, in yet a further aspect the invention provides a plant growth inhibiting, plant damaging, or plant killing composition for use in soya crops comprising the compound of formula (I) as hereinbefore defined and an inert carrier or diluent.

Compositions containing the compound of formula (I) include both dilute compositions, which are ready for immediate use, and concentrated compositions, which require to be diluted before use, usually with water. Preferably the compositions contain from 0.01% to 90% by weight of the active ingredient. Dilute compositions ready for use preferably contain from 0.01% to 2% of active ingredient, while concentrated compositions may contain from 20% to 90% of active ingredient, although from 20% to 70% is usually preferred.

The solid compositions may be in the form of granules, or dusting powders wherein the active ingredient is mixed with a finely divided solid diluent, e.g. kaolin, bentonire, kieselguhr, dolomite, calcium carbonate, talc, powdered magnesia, Fuller's earth and gypsum. They may also be in the form of dispersible powders or grains, comprising a wetting agent to facilitate the dispersion of the powder or grains in liquid. Solid compositions in the form of a powder may be applied as foliar dusts.

Liquid compositions may comprise a solution or dispersion of the active ingredient in water optionally containing a surface-active agent, or may comprise a solution or dispersion of an active ingredient in a water-immiscible organic solvent which is dispersed as droplets in water.

Surface-active agents may be of the cationic, anionic, or non-ionic type or mixtures thereof. The cationic agents are, for example, quaternary ammonium compounds (e.g. cetyltrimethylammonium bromide). Suitable anionic agents are soaps; salts of aliphatic mono ester of sulphuric acid, for example sodium lauryl sulphate; and salts of sulphonated aromatic compounds, for example sodium dodecylbenzenesulphonate, sodium, calcium, and ammonium lignosulphonate, butylnaphthalene sulphonate, and a mixture of the sodium salts of diisopropyl and triisopropylnaphthalenesulphonic acid. Suitable non-ionic agents are the condensation products of ethylene oxide with fatty alcohols such as oleyl alcohol and cetyl alcohol, or with alkylphenols such as octyl- or nonyl- phenol (e.g. Agral 90) or octyl-cresol. Other non-ionic agents are the partial esters derived from long chain fatty acids and hexitol anhydrides, for example sorbitan monolaurate; the condensation products of the partial ester with ethylene oxide; the lecithins; and silicone surface active agents (water soluble surface active agents having a skeleton which comprises a siloxane chain e.g. Silwet L77). A suitable mixture in mineral oil is for example Atplus 411F.

The aqueous solutions or dispersions may be prepared by dissolving the active ingredient in water or an organic solvent optionally containing wetting or dispersing agent(s) and then, when organic solvents are used, adding the mixture so obtained to water optionally containing wetting or dispersing agent(s). Suitable organic solvents include, for example, ethylene di-chloride, isopropyl alcohol, propylene glycol, diacetone alcohol, toluene, kerosene, methylnaphthalene, the xylenes and trichloroethylene.

The compositions for use in the form of aqueous solutions or dispersions are generally supplied in the form of a concentrate containing a high proportion of the active ingredient, and the concentrate is then diluted with water before use. The concentrates are usually required to withstand storage for prolonged periods and after such storage, to be capable of dilution with water to form aqueous preparations which remain homogeneous for a sufficient time to enable them to be applied by conventional spray equipment. Concentrates conveniently contain 20–90%, preferably 20–70%, by weight of the active ingredient(s). Dilute preparations ready for use may contain varying amounts of the active ingredient(s) depending upon the intended purpose; amounts of 0.01% to 10.0% and preferably 0.1% to 2%, by weight of active ingredient(s) are normally used.

A preferred form of concentrated composition comprising the active ingredient which has been finely divided and which has been dispersed in water in the presence of a surface-active agent and a suspending agent. Suitable suspending agents are hydrophilic colloids and include, for example, polyvinylpyrrolidone and sodium carboxymethylcellulose, and the vegetable gums, for example gum acacia and gum tragacanth. Preferred suspending agents are those which impart thixotropic properties to, and increase the viscosity of the concentrate. Examples of preferred suspending agents include hydrated colloidal mineral silicates, such as montmorillonite, beidellite, nontronite, hectorite, saponite, and saucorite. Bentonite is especially preferred. Other suspending agents include cellulose derivatives and polyvinyl alcohol.

The rate of application of the compound of the invention will depend on a number of factors including, for example, the identity of the plants whose growth is to be inhibited, the formulations selected for use and whether the compound is to be applied for foliage or root uptake. As a general guide, however, an application rate of from 0.01 to 10 kilograms per hectare is generally suitable while up to 0.8 kilograms per hectare may be preferred. In particular rates of up to 0.5 kilograms per hectare are useful. More preferably rates of from 0.01 to 0.25 kilogram per hectare and most preferably rates of from 0.01 to 0.2 kilogram per hectare are used.

The compositions of the invention may comprise, in addition to the compound of formula (I) one or more compounds not of the invention but which possess biological activity for example herbicides, fungicides, insecticides (optionally with an insecticide synergist) and plant growth regulators. Accordingly in yet a still further embodiment the invention provides a herbicidal composition comprising a mixture of a herbicidal compound of formula (I) as hereinbefore defined with at least one other herbicide.

The other herbicide may be any herbicide not having the formula (I). It will generally be a herbicide having a complementary action in the particular application.

Examples of useful complementary herbicides include:

A. benzo-2,1,3-thiadiazin-4-one-2,2-dioxides such as bentazone;

B. hormone herbicides, particularly the phenoxy alkanoic acids such as MCPA, MCPA-thioethyl, dichlorprop, 2,4,5-T, MCPB, 2,4-D, 2,4-DB, mecoprop, trichlopyr, fluroxypyr, clopyralid, and their derivatives (eg. salts, esters and amides);

C. 1,3 dimethylpyrazole derivatives such as pyrazoxyfen, pyrazolate and benzofenap;

D. Dinitrophenols and their derivatives (eg. acetates) such as dinoterb, dinoseb and its ester, dinoseb acetate;

E. dinitroaniline herbicides such as dinitramine, trifluralin, ethalflurolin, pendimethalin, oryzalin;

F. arylurea herbicides such as diuron, flumeturon, metoxuron, neburon, isoproturon, chlorotoluron, chloroxuron, linuron, monolinuron, chlorbromuron, daimuron, methabenzthiazuron;

G. phenylcarbamoyloxyphenylcarbamates such as phenmedipham and desmedipham;

H. 2-phenylpyridazin-3-ones such as chloridazon and norflurazon;

I. uracil herbicides such as lenacil, bromacil and terbacil;

J. triazine herbicides such as atrazine, simazine, aziprotryne, cyanazine, prometryn, dimethametryn, simetryne, and terbutryn;

K. phosphorothioate herbicides such as piperophos, bensulide, and butamifos;

L. thiocarbamate herbicides such as prosulfocarb, cycloate, vernolate, molinate, thiobencarb, butylate*, EPTC*, tri-allate, di-allate, esprocarb, tiocarbazil, pyridate, and dimepiperate;

* These compounds are preferably employed in combination with a safener such as dichlormid.

M. 1,2,4-triazin-5-one herbicides such as metamitron and metribuzin;

N. benzoic acid herbicides such as 2,3,6-TBA, dicamba and chloramben;

O. anilide herbicides such as pretilachlor, butachlor, alachlor, propachlor, propanil, metazachlor, metolachlor, acetochlor, and dimethachlor;

P. dihalobenzonitrile herbicides such as dichlobenil, bromoxynil and ioxynil;

Q. haloalkanoic herbicides such as dalapon, TCA and salts thereof;

R. diphenylether herbicides such as lactofen, fluroglycofen or salts or ester thereof, nitrofen, bifenox, aciflurofen and salts and esters thereof, oxyfluorfen, fomesafen, chlornitrofen and chlomethoxyfen;

S. aryloxyphenoxypropionate herbicides such as diclofop and esters thereof such as the methyl ester, fluazifop and esters thereof, haloxyfop and esters thereof, quizalofop and esters thereof and fenoxaprop and esters thereof such as the ethyl ester;

T. cyclohexanedione herbicides such as alloxydim and salts thereof, sethoxydim, cycloxydim, tralkoxydim, and clethodim;

U. sulfonyl urea herbicides such as chlorsulfuron, sulfometuron, metsulfuron and esters thereof; bensulfuron and esters thereof such as DPX-M6313, chlorimuron and esters such as the ethyl ester thereof pirimisulfuron and esters such as the methyl ester thereof, 2-[3-(4-methoxy-6-methyl-1,3, 5-triazin-zyl)-3-methylureidosulphonyl) benzoic acid esters such as the methyl ester thereof (DPX-L5300) and pyrazosulfuron;

V. imidazolidinone herbicides such as imazaquin, imazamethabenz, imazapyr and isopropylammonium salts thereof, imazethapyr;

W. arylanilide herbicides such as flamprop and esters thereof, benzoylprop-ethyl, diflufenican;

X. amino acid herbicides such as glyphosate and glufosinate and their salts and esters, sulphosate and bialaphos;

Y. organoarsenical herbicides such as monosodium methanearsonate (MSMA);

Z. herbicidal amide derivative such as napropamide, propyzamide, carbetamide, tebutam, bromobutide, isoxaben, naproanilide and naptalam;

AA. herbicidal triketones such as sulcotrione;

AB. miscellaneous herbicides including ethofumesate, cinmethylin, difenzoquat and salts thereof such as the methyl sulphate salt, clomazone, oxadiazon, bromofenoxim, barban, tridiphane, flurochloridone, quinclorac, dithiopyr and mefanacet;

AC. Examples of useful contact herbicides include: bipyridylium herbicides such as those in which the active entity is paraquat and those in which the active entity is diquat;

The following example illustrates the invention.

Biological Data

The herbicidal activity of the compound was tested as follows:

The chemical was formulated by dissolving it in an appropriate amount, dependent on the final spray volume, of a solvent/surfactant blend which comprised 78.2 gm/litre of Tween 20 and 21.8 gm/litre of Span 80 adjusted to 1 litre using methylcyclohexanone. Tween 20 is a Trade Mark for a surface-active agent comprising a condensate of 20 molar proportions of ethylene oxide with sorbitan laurate. Span 80 is a Trade Mark for a surface-active agent comprising sorbitan mono-laurate. If the chemical did not dissolve, the volume was made up to 5cm$^3$ with water, glass beads were added and this mixture was then shaken to effect dissolution or suspension of the chemical, after which the beads were removed. In all cases, the mixture was then diluted with water to the required spray volume. If sprayed independently, volumes of 10 cm$^3$ and 14 cm$^3$ were required for pre-emergence and post-emergence tests respectively; if sprayed together, 20 cm$^3$ was required. The sprayed aqueous emulsion contained 4% of the initial solvent/surfactant mix and the test chemical at an appropriate concentration.

The spray compositions so prepared were sprayed onto young pot plants (post-emergence test) at a spray volume equivalent to 400 litres per hectare. Damage to plants was assessed 13 days after spraying for the post-emergence test by comparison with untreated plants, on a scale of 0 to 9 where 0 is 0% damage, 1 is 1–5% damage, 2 is 6–15% damage, 3 is 16–25% damage, 4 is 26–35% damage, 5 is 36–59% damage, 6 is 60–69% damage, 7 is 70–79% damage, 8 is 80–89% damage and 9 is 90–100% damage.

In a test carried out to detect pre-emergence herbicidal activity, crop seeds were sown at 2 cm depth (i.e. maize, soya) and weed seeds at 1 cm depth beneath compost and sprayed with the compositions at a spray volume equivalent to 400 litres per hectare. 20 days after spraying, the seedlings in the sprayed plastic trays were compared with the seedlings in unsprayed control trays, the damage being assessed on the same scale of 0 to 9.

The results of the tests are given in Table I.

TABLE III

Abbreviations used for Test Plants

GM — *Glycine max* (Soyabean)
ZM — *Zea mays* (Corn)
PA — *Polygonum aviculare*
MI — *Matricaria perforata*
CA — *Chenopodium album*
AR — *Amaranthus retroflexus*
GA — *Galium aparine*
EH — *Euphorbia heterophylla*
IH — *Ipomoea hederacea*
XT — *Xanthium strumarium*
AF — *Avena fatua*
AM — *Alopecurus myosuroides*
AE — *Agropyron repens*
SH — *Sorghum halepense*
SV — *Setaria viridis*
BP — *Brachiaria platyphylla*
PD — *Panicum dicotomiflorum*

TABLE I

| Rate of appln g/ha | Pre/Post | GM | ZM | PA | MI | CA | AR | GA | EH | IH | AT | XI | AF | MM | SH | SV | RP | PD | EC | CE |
|---|---|---|---|---|---|---|---|---|---|---|---|---|---|---|---|---|---|---|---|---|
| 62.5 | Pre | 0 | 3 | 9 | 9 | 9 | 9 | 6 | 9 | 8 | 9 | 3 | 4 | 9 | 9 | 9 | 9 | 9 | 9 | 0 |
|  | Post | 6 | 3 | 9 | 9 | 9 | 9 | 9 | 9 | 9 | 9 | 9 | 5 | 5 | 6 | 7 | 9 | 9 | 6 | 3 |

In a further test the activity of compound (I) as a pre-emergence treatment was compared to that of a compound of formula (A) and a compound of formula (B). The test was conducted as follows:

Each chemical was formulated by dissolving it in a solvent/surfactant blend which comprised 49.75% acetone, 49.75% water and 0.5% of Tween 20. All seeds were sown at half an inch depth beneath compost and sprayed with 20 ml of the compositions at a spray volume equivalent to 200 litres per hectare. Damage to plants was assessed 20 days after spraying by comparison with untreated plants and the results recorded as percent damage.

The results of the test are given in Table II.

TABLE III-continued

Abbreviations used for Test Plants

EC — *Echinochloa crus-galli*
CE — *Cyperus esculentus*
AT — *Abutilon threophrasti*
SS — *Sida spinosa*
SN — *Solanum nigrum*
SF — *Setaria faberii*
SL — *Setaria lutescens*
DS — *Digitaria sanguinalis*
PM — *Panicum miliaceum*
SU — *Sorghum vulgare*

TABLE II

| COMPOUND | g Appln Rate/Ha | GM | XT | IP | AT | CA | AR | SS | SN | SF | SV | SL | EC | DS | PD | PM | SH | SU | BP |
|---|---|---|---|---|---|---|---|---|---|---|---|---|---|---|---|---|---|---|---|
| I | 32 | 0 | 0 | 3 | 96 | 100 | 100 | 98 | 100 | 100 | 100 | 96 | 62 | 100 | 100 | 88 | 52 | 42 | 91 |
|  | 63 | 4 | 0 | 13 | 100 | 100 | 100 | 100 | 100 | 100 | 100 | 98 | 91 | 100 | 100 | 100 | 72 | 72 | 100 |
|  | 125 | 3 | 18 | 94 | 100 | 100 | 100 | 100 | 100 | 100 | 100 | 100 | 100 | 100 | 100 | 100 | 100 | 100 | 100 |
|  | 250 | 18 | 12 | 98 | 100 | 100 | 100 | 100 | 100 | 100 | 100 | 100 | 100 | 100 | 100 | 100 | 100 | 100 | 100 |
| A | 32 | 5 | 0 | 0 | 38 | 100 | 100 | 77 | 99 | 48 | 63 | 33 | 27 | 62 | 90 | 17 | 8 | 8 | 18 |
|  | 63 | 0 | 0 | 2 | 88 | 100 | 100 | 93 | 100 | 78 | 88 | 65 | 47 | 100 | 100 | 55 | 17 | 15 | 58 |
|  | 125 | 3 | 0 | 8 | 98 | 100 | 100 | 100 | 100 | 100 | 100 | 94 | 73 | 100 | 100 | 100 | 58 | 58 | 92 |
|  | 250 | 3 | 0 | 55 | 100 | 100 | 100 | 100 | 100 | 100 | 100 | 99 | 99 | 100 | 100 | 100 | 94 | 95 | 100 |
| B | 32 | 3 | 0 | 0 | 42 | 3 | 43 | 47 | 78 | 15 | 20 | 17 | 7 | 3 | 12 | 0 | 3 | 3 | 2 |
|  | 63 | 3 | 0 | 3 | 72 | 22 | 100 | 90 | 100 | 58 | 69 | 42 | 17 | 22 | 80 | 33 | 12 | 10 | 7 |
|  | 125 | 0 | 0 | 15 | 80 | 97 | 100 | 96 | 100 | 99 | 99 | 83 | 52 | 99 | 100 | 96 | 23 | 18 | 83 |
|  | 250 | 0 | 0 | 15 | 100 | 100 | 100 | 100 | 100 | 100 | 100 | 100 | 91 | 100 | 100 | 100 | 82 | 68 | 100 |

CHEMICAL FORMULAE (IN DESCRIPTION)

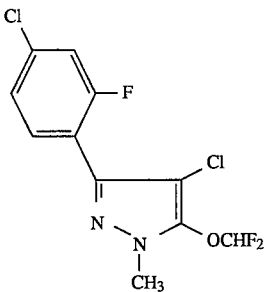

(A)

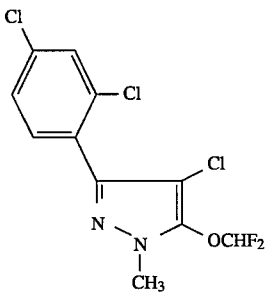

(B)

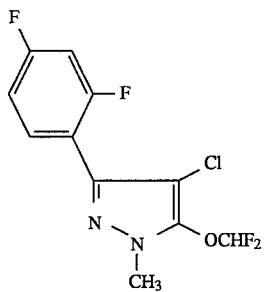

We claim:

1. A method for killing or controlling weeds in a soya crop, which method comprises applying to the crop or to the location thereof a compound of formula (I):

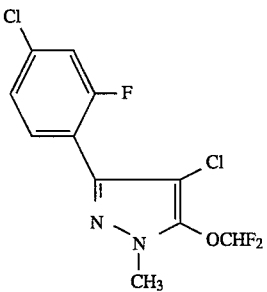

in an amount sufficient to kill the weeds but insufficient to kill the crop.

2. A method according to claim 1 wherein the compound of formula (I) is applied at 0.01 to 0.5 kilograms per hectare.

3. A method according to claim 2 wherein the compound of formula (I) is applied at 0.01 to 0.25 kilograms per hectare.

4. A method according to claim 1 wherein the weeds are Ipomoea species, Amaranthus species, Datura species, Euphorbia species, Sida species, Setaria species, Echinochloa species, Sorghum species, Brachiaria species, Panicum species, Solanum species, Digitaria species, Xanthium species, Polygonum species, *Chenopodium album* and *Abutilon threophrasti*.

5. A method according to claim 4 wherein the weeds are *Abutilon threophrasti, Euphorbia heterophylla,* Ipomoea species, *Chenopodium album, Amaranthus retroflexus, Sida spinosa, Solanum nigrum, Setaria faberii, Setaria viridis, Echinochloa crus-galli, Digitaria sanguinalis, Panicum dicotomiflorum, Panicum miliaceum, Sorghum halepense, Brachiaria platyphylla, Sorghum vulgare* and *Setaria lutescens*.

6. A method according to claim 1 wherein the compound of formula (I) is applied as a pre-emergence treatment.

7. A method according to claim 2 wherein the weeds are Ipomoea species, Amaranthus species, Datura species, Euphorbia species, Sida species, Setaria species, Echinochloa species, Sorghum species, Brachiaria species, Panicum species, Solanum species, Digitaria species, Xanthium species, Polygonum species, *Chenopodium album* and *Abutilon threophrasti*.

8. A method according to claim 7 wherein the weeds are *Abutilon threophrasti, Euphorbia heterophylla,* Ipomoea species, *Chenopodium album, Amaranthus retroflexus, Sida spinosa, Solanum nigrum, Setaria faberii, Setaria viridis, Echinochloa crus-galli, Digitaria sanguinalis, Panicum dicotomiflorum, Panicum miliaceum, Sorghum halepense, Brachiaria platyphylla, Sorghum vulgate* and *Setaria lutescens*.

9. A method according to claim 3 wherein the weeds are Ipomoea species, Amaranthus species, Datura species, Euphorbia species, Sida species, Setaria species, Echinochloa species, Sorghum species, Brachiaria species, Panicum species, Solanum species, Digitaria species, Xanthium species, Polygonum species, *Chenopodium album* and *Abutilon threophrasti*.

10. A method according to claim 9 wherein the weeds are *Abutilon threophrasti, Euphorbia heterophylla,* Ipomoea species, *Chenopodium album, Amaranthus retroflexus, Sida spinosa, Solanum nigrum, Setaria faberii, Setaria viridis, Echinochloa crus-galli, Digitaria sanguinalis, Panicum dicotomiflorum, Panicum miliaceum, Sorghum halepense, Brachiaria platyphylla, Sorghum vulgate* and *Setaria lutescens*.

11. A method according to claim 2 wherein the compound of formula (I) is applied as a pre-emergence treatment.

12. A method according to claim 3 wherein the compound of formula (I) is applied as a pre-emergence treatment.

13. A method according to claim 4 wherein the compound of formula (I) is applied as a pre-emergence treatment.

14. A method according to claim 5 wherein the compound of formula (I) is applied as a pre-emergence treatment.

15. A method according to claim 7 wherein the compound of formula (I) is applied as a pre-emergence treatment.

16. A method according to claim 8 wherein the compound of formula (I) is applied as a pre-emergence treatment.

17. A method according to claim 9 wherein the compound of formula (I) is applied as a pre-emergence treatment.

18. A method according to claim 10 wherein the compound of formula (I) is applied as a pre-emergence treatment.

19. A method for killing or controlling weeds in a soya or corn crop, comprising applying to the crop or to the location thereof a compound of formula (I):

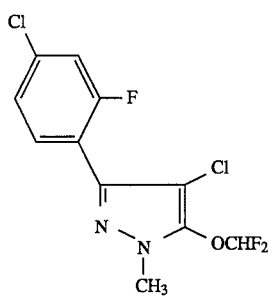
(I)
in an amount sufficient to kill the weeds but insufficient to kill the crop.
20. A method according to claim 19, wherein the compound of formula (I) is applied at 0.01 to 0.25 kilograms per hectare.
21. A method according to claim 19, wherein the compound of formula (I) is applied at 0.01 to 0.125 kilograms per hectare.
* * * * *